United States Patent [19]

Ostermayer, Jr.

[11] 4,278,353
[45] Jul. 14, 1981

[54] OPTICAL INSPECTION OF GOLD SURFACES

[75] Inventor: Frederick W. Ostermayer, Jr., Chatham, N.J.

[73] Assignee: Bell Telephone Laboratories, Incorporated, Murray Hill, N.J.

[21] Appl. No.: 139,172

[22] Filed: Apr. 11, 1980

[51] Int. Cl.³ .......................... G01J 3/48; G01N 21/55
[52] U.S. Cl. ..................................... 356/416; 356/448
[58] Field of Search ................................ 356/445–448, 356/402, 408, 425, 416; 250/226

[56] References Cited

U.S. PATENT DOCUMENTS

| Re. 29,031 | 11/1976 | Irving et al. | 356/178 X |
| 3,327,584 | 6/1967 | Kissinger | 356/375 |
| 4,120,591 | 10/1978 | van Valkenburg | 356/178 X |

OTHER PUBLICATIONS

Cheh et al., "Electrochemical and Structural Aspects of Gold Electrodeposition from Dilute Solutions by Direct Current", *Journal of the Electrochemical Society*, vol. 118, No. 11, pp. 1737–1747, (1971).
Birth, G. S., "A Fiber Optics Reflectance Attachment", *Agricultural Engineering*, Aug. 1967, pp. 448, 449.

Jenkins et al., *Fundamentals of Optics*, N.Y., 1957, Third Edition, p. 522.
Born et al., *Principles of Optics*, Third (Revised Ed) p. 661.
Sard et al., "Some Properties of Electroless Gold Deposits", *Plating*, vol. 58, pp. 893–900 (1971).

*Primary Examiner*—John K. Corbin
*Assistant Examiner*—Bruce Y. Arnold
*Attorney, Agent, or Firm*—Peter V. D. Wilde

[57] ABSTRACT

Gold plated surfaces are inspected by means of reflected light in the wavelength range of 450 to 575 nanometers to give a sensitive indication of surface conditions. This test automates the visual inspection for "brown gold" and is advantageously used in continuous strip gold plating operations. The technique may be used as a quality control check or as a process control to correct non-optimum process parameters that lead to degradation of gold surface conditions. In a preferred embodiment, the reflected light from the surface being inspected is compared with light reflected from a reference surface. Alternately, a separate wavelength band, typically 700 to 800 nanometers, is reflected from the surface being inspected and compared to the reflected light in the 450 to 575 nanometer wavelength band.

10 Claims, 4 Drawing Figures

OPTICAL FIBER BUNDLE REFLECTOMETER

FIBER REFLECTOMETER REFLECTIVITY RELATIVE TO SAMPLE I

OPTICAL INSPECTION OF GOLD SURFACES

BACKGROUND OF THE INVENTION

1. Field of the Invention

This invention relates to determining the condition of a gold surface by means of optical reflection.

2. Description of the Prior Art

In the gold electroplating art, a typical quality control check is a visual inspection of a gold plated article for discolored or "burnt" deposits, known as "brown gold". With the advent of continuous high-speed strip line gold plating apparatus, it has become desirable to automate the inspection of gold plated surfaces; see, for example, the plating apparatus described in U.S. Pat. No. 4,153,523 assigned to the same assignee as the present invention. In addition, the visual inspection of gold plated objects typically results in less than uniform results, with inspection by different persons resulting in slightly different levels of acceptability.

It is known that the degree of surface roughness of gold deposits affects the characteristics of the reflected light; see, for example, "Electrochemical And Structural Aspects of Gold Electrodeposition From Dilute Solutions By Direct Current", by H. Y. Cheh and R. Sard in *Journal Of The Electrochemical Society*, Vol. 118, pages 1737–1747, (1971). However, the prior art studies of specular reflectivity did not correlate very well with the surface conditions monitored by visual quality control checks.

It is therefore desirable to have an automated high-speed method of detecting surface imperfections on plated gold surfaces that gives an accurate and reliable indication of unacceptable surface conditions.

SUMMARY OF THE INVENTION

I have invented an optical method of detecting surface conditions on gold surfaces by means of reflected light. In this method, illumination from an optical source is directed at a gold surface. Reflected light substantially in the wavelength range of 450 to 575 nanometers is detected by means of an optical detector, with the output giving an indication of the condition of the surface. In one embodiment, the output is compared to a reference value determined by the reflected light from a reference surface having known characteristics. In another embodiment, the light in the above-mentioned wavelength range is compared to light having wavelengths greater than 700 nanometers that is reflected from the same gold surface to compensate for differences not related to relevant surface conditions. In a preferred embodiment, a bundle of parallel optical fibers is used to conduct illumination from the source to the gold surface and to conduct reflected light from the gold surface to the detector.

DETAILED DESCRIPTION

Figure 1:
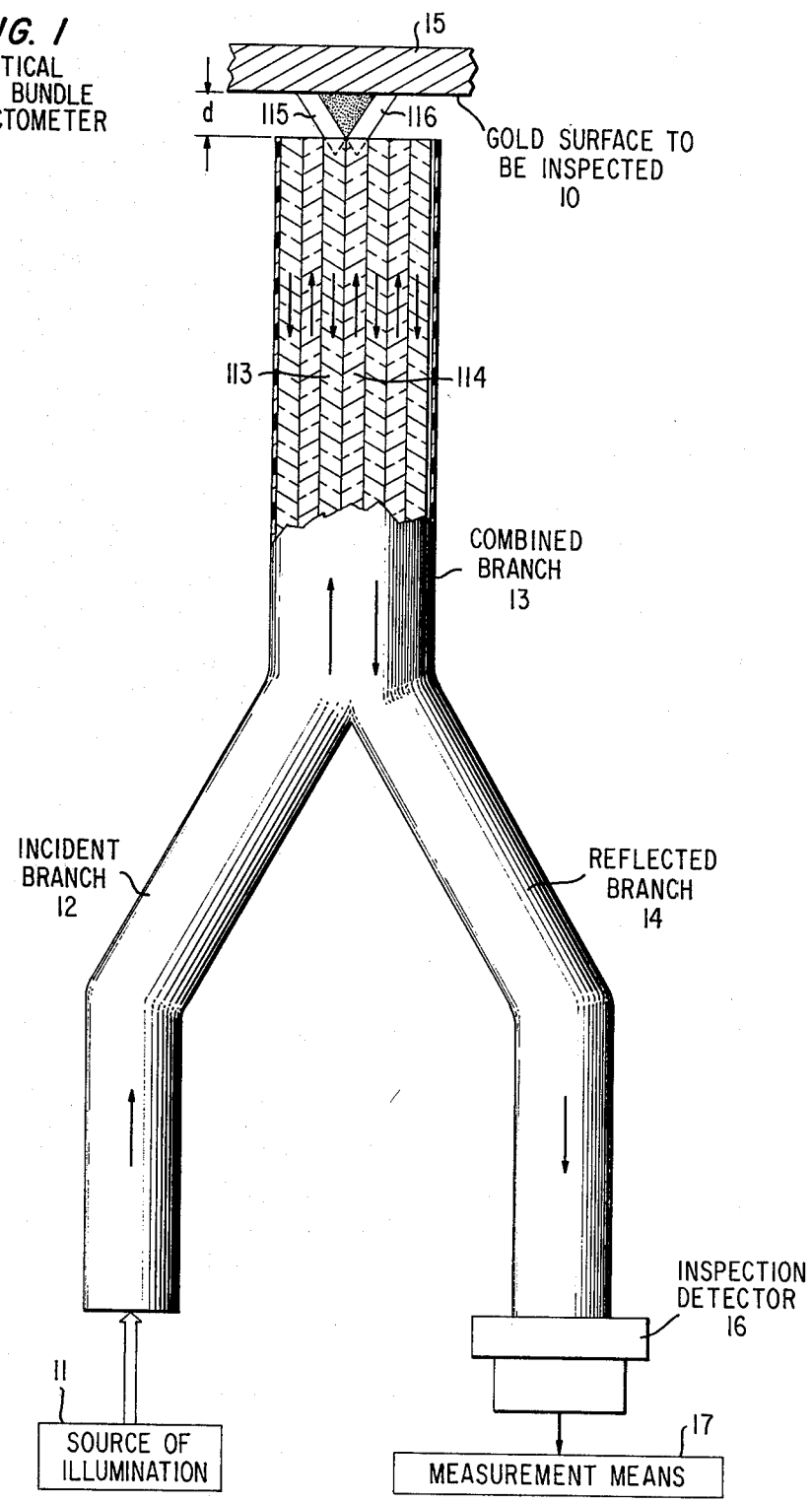
FIG. 1 shows a first embodiment of the inventive technique wherein the amplitude of light reflected from the inspected article is determined.

The following description relates to a method of inspecting gold surfaces, typically for use as a process control or a quality control check for a gold electroplating operation. Referring to FIG. 1, a gold surface to be inspected (10) is placed a distance d from the end of an optical fiber bundle. This bundle comprises optical fibers transmitting both incident light to the surface (113) and reflected light from the surface (114). The incident illumination fibers branch off to a source of illumination (11), while the reflected illumination fibers branch off to a detector (16) as shown. The detector in turn is connected to a meter or other output measuring means (17), which gives an indication of the amount of illumination incident on the detector.

The operation of the device is illustrated with the gold surfaces of five samples, as indicated in Table I. These samples were obtained by electroplating gold at various current densities from a cyanide electrolyte onto a copper substrate, with a small amount of cobalt (less than 1 percent) being included as a gold hardening agent. The surfaces on these samples have an appearance ranging from bright yellow for sample I to matte brown for sample V. The samples are listed in increasing order of discoloration, as determined by the criteria of standard visual quality control checks. The experience of the gold electroplating industry has shown that significant discoloration is an indication of non-optimum plating conditions or non-optimum substrate conditions. Such non-optimum conditions frequently, although not always, indicate that the subsequent performance of the gold electroplated article will be unacceptable. Typically, for use as electrical contacts, samples I, II, and III are acceptable, with samples IV and V being unacceptable. However, the level of acceptability depends upon the intended application and other considerations.

TABLE I

| Sample No. | Appearance |
|---|---|
| I | Bright Yellow |
| II | Smooth Yellow |
| III | Matte Yellow |
| IV | Matte Yellowish Brown |
| V | Matte Brown |

Figure 4:
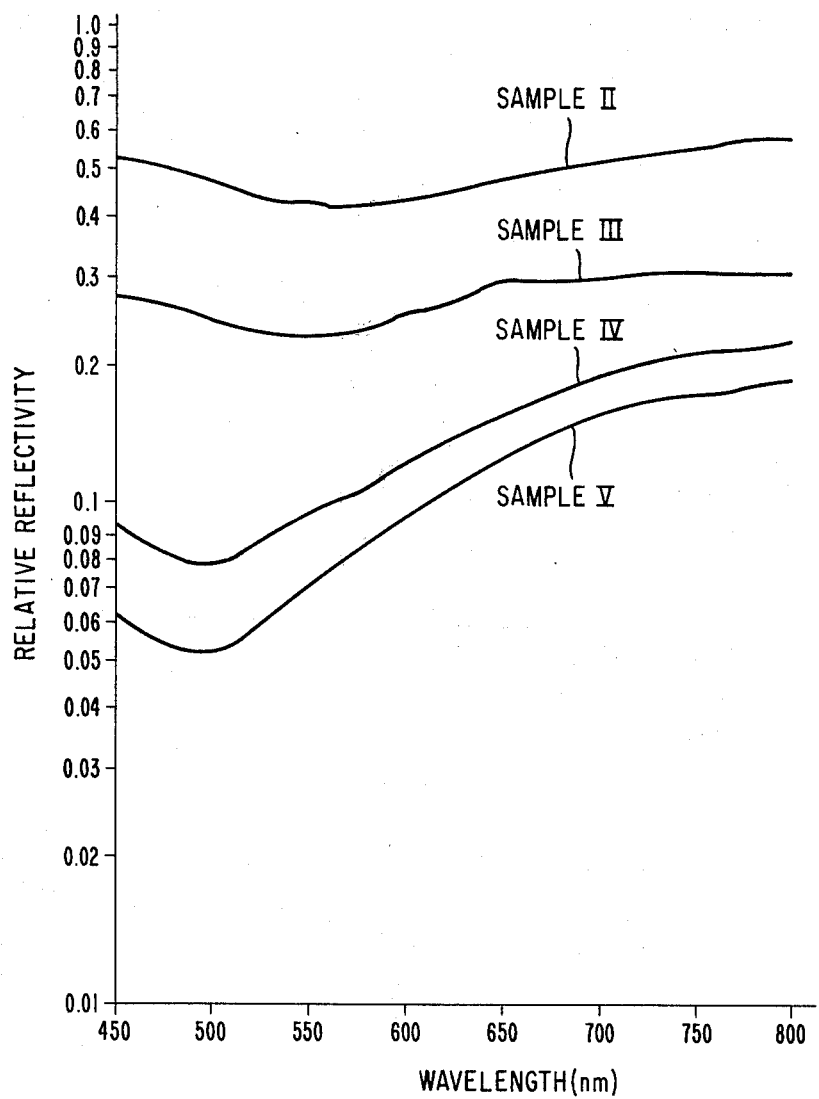
FIG. 4 shows typical fiber reflectometer measurements.

A graph of the reflectivity of samples II–V relative to the reflectivity of sample I versus the wavelength of the illumination is shown in FIG. 4. This data was obtained with the fiber reflectometer of FIG. 1, wherein the source was a tungsten lamp and monochromator. Sample I is considered to be a substantially perfect gold surface that meets quality control standards for gold electroplating. As can be seen, samples II, III, IV, and V have substantially lower reflectivities, particularly in the portion of the spectrum between approximately 450 and 575 nanometers.

It has been determined that the anomalous dip in the relative reflectivity in the range of approximately 450 to 575 nanometers, and the especially about 475–550 nanometers, is characteristic of "brown gold", and is due to Rayleigh scattering by particles or projections on the surface; see, for example, *Principles Of Optics*, by M. Born and E. Wolf, third revised edition, page 661. It is significant that the fiber optic bundle detects both specular reflections and diffuse reflections from the gold surface. Previous studies of gold surfaces using only specular reflections, that is, the reflections wherein the angle of reflection equals the angle of incidence, have not noted this wavelength dependence; see, for example, the article by H. Y. Cheh and R. Sard, noted above. It has been found necessary to include diffuse reflections, that is, the reflections wherein the incident light is scatttered over a wide range of angles, to obtain the above-noted effect. Apparently, this is because the specular reflections are affected by macroscopic surface conditions; that is, by surface features that are large compared to the wavelength of the incident light. Such effects are minimized when diffuse reflections are also detected.

A sufficient proportion of diffuse reflections is obtained when the angle of the cone of illumination from the source is at least 20 degrees, or when the angle of the cone of acceptance of the detector is at least 20 degrees. If optical fibers are used, the angles of cones 115 and 116 as shown in FIG. 1 are considered to be the angles of acceptance and illumination, respectively. The angles of these cones are measured as the full width half maximum values. The cones are typically circular in cross-section, but could be other shapes. Measurements of total reflectivity in an ellipsoidal reflectometer (not shown) show that the sensitivity to brown gold in the 450–575 nanometer range is reduced when all diffuse reflections are detected. Thus, the optical fiber reflectometer arrangement noted above gives an approximately optimum ratio of diffuse to specular reflections.

Figure 2:
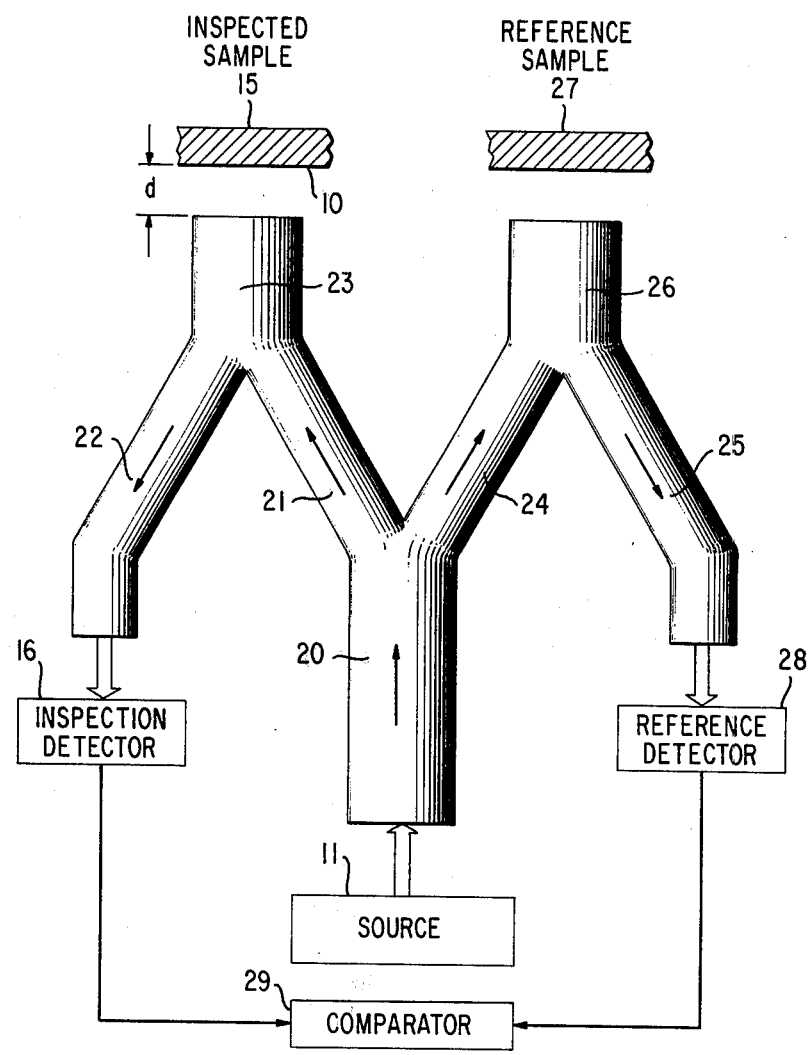
FIG. 2 shows a second embodiment of the inventive technique wherein light reflected from the inspected article is compared to light reflected from a reference article.

It can thus be seen that for the first time an instrumented measurement of the condition of a gold surface that relates to brown staining is obtained. For production line use, it is desirable to compensate for changes in various components of the measurement system, including the transmissivity of the path from the end of the fiber bundle to the test sample. Referring to FIG. 2, a second embodiment is shown wherein light from the source is directed both to the inspected sample (15) and to a reference sample (27) having a known reflectivity. Typically, the reference sample is a highly reflective gold surface such as sample I above. Light from the inspected sample is detected by inspection detector 16, whereas light reflected from the reference sample is detected by reference detector 28. The outputs of these detectors are compared in a comparator (29) to determine whether the inspected sample is of acceptable quality. The comparator typically takes the difference or the ratio of the outputs of the two detectors and provides a "pass" indication if the output of inspection detector 16 is within an acceptable range of the output of reference detector 28, and provides a "fail" indication if the output of detector 16 is below that range.

Figure 3:
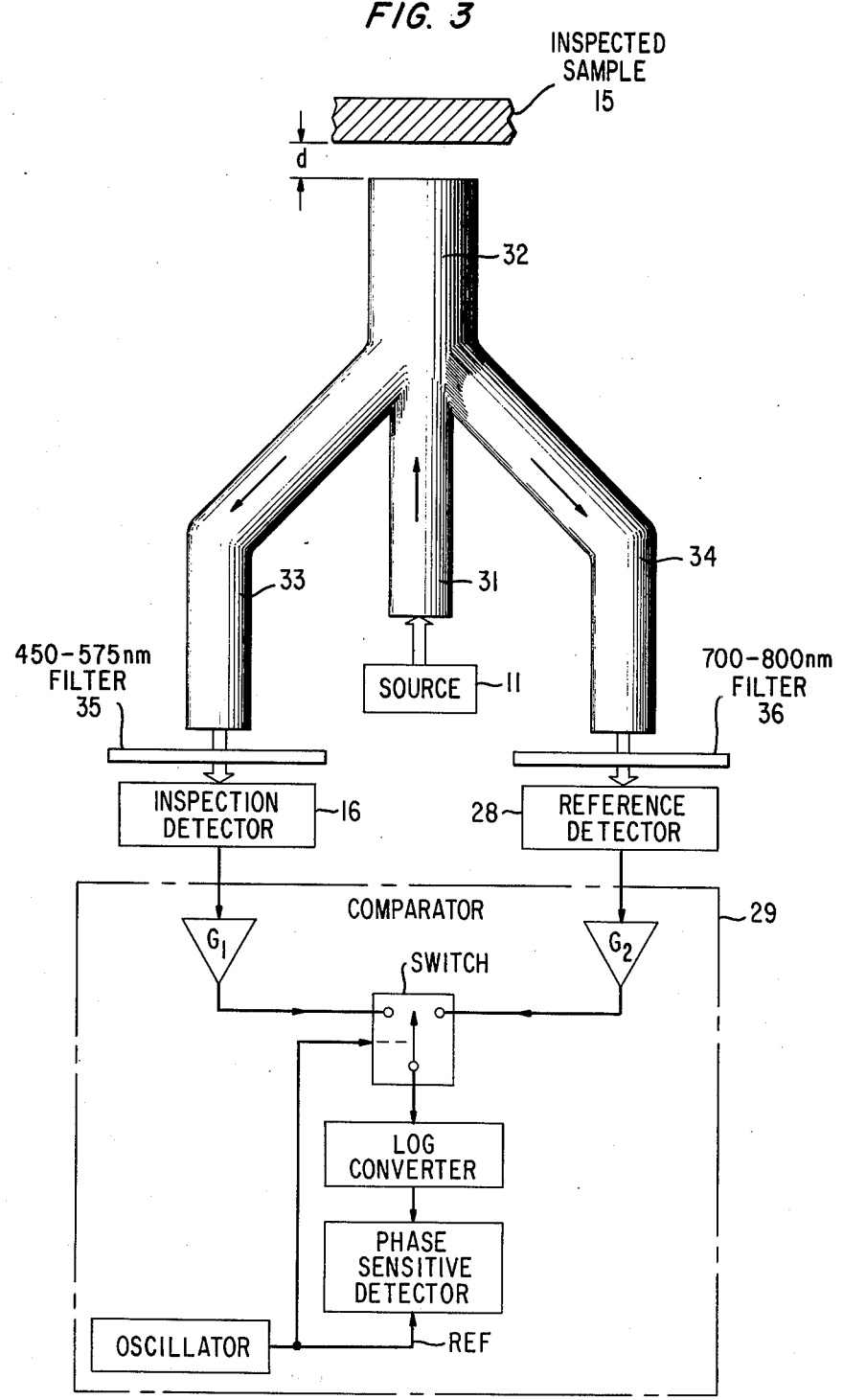
FIG. 3 shows a third embodiment of the inventive technique, wherein reflected light in two wavelength ranges is compared.

A third preferred embodiment is shown in FIG. 3 wherein the reflectivities in two wavelength ranges are compared for a single sample. A broadband light source (11), typically being a tungsten lamp, illuminates the sample. A first portion of the reflected light is directed along branch 33 to inspection detector 16 operating in the range of 450 to 575 nanometers. A second portion of the reflected light is directed along branch 34 to reference detector 28 operating at wavelengths greater than 700 nanometers and typically in the range of 700 to 800 nanometers. It can be seen from FIG. 4 that these longer wavelengths show much less variability due to the surface conditions noted. By comparing the outputs of these two detectors, a pass-fail indication can be obtained. This corrects for variations in the optical system while requiring only the inspected sample to be measured. As before, the comparison may be made by simply subtracting the output of one detector from the output of the other detector. However, it is also possible to take the ratio of the outputs of the two detectors, with the pass condition indicating that the output of the inspection detector is within an acceptable range of the output of the reference detector. A typical comparator arrangement (29) is shown, with others being possible.

The above embodiments are more fully explained by means of the following example.

EXAMPLE

In the embodiments of FIG. 1 the source used is a gallium phosphide light emitting diode (LED) producing a yellow-green output (Western Electric 530 B). The lens of the LED was removed to allow better light coupling to the optical fiber bundle, and the LED was butted directly against the fiber bundle. The peak output of this LED is approximately 560 nanometers. The output falls to approximately one-half the peak value at 550 and 575 nanometers. The detector is a planar diffused silicon PIN photodiode. The maximum spectral response is at approximately 850 nanometers, with the response at 560 nanometers being approximately 70 percent of the maximum (PIN-10DP United Detector Technology, Inc.). The optical fiber is a bundle of approximately 400 individual fibers having diameters of approximately 0.076 millimeters (Dolan-Jenner Industries, type EK 15). The diameter of the branches of the bundle is approximately 1.2 millimeters, whereas the diameter of the combined bundle is approximately 1.6 millimeters. The individual fibers carrying the transmitted and reflected light are randomly scattered throughout the combined bundle. The transmission spectrum of this fiber bundle is at maximum at about 520 nanometers. The cone of acceptance of each fiber in the bundle (115) is approximately 67 degrees. The cone of illumination from each of the fibers carrying transmitted light (116) is also approximately 67 degrees with the LED source used. The output of the photodetector is a maximum to the light from the light emitting diode when the spacing d is approximately 0.25 millimeters. The distance d which produces maximum output depends, among other things, on the aforementioned angle of the cone of illumination and the angle of the cone of acceptance of the optical fibers used. Although a certain variation in spacing is possible, it is desirable to operate at the spacing producing maximum output. This minimizes the variation in the reflected light due to small variations in the distance from the sample, as may occur on a production line. In the present example, a spacing from 0.125 to 0.50 millimeters produces an output level within 10 percent of the maximum, obtained at 0.25 millimeters, for all five samples of Table I. The sensitivity of this arrangement is such that the "acceptable" samples II and III produce an inspection detector output that is within a factor of 5 of the output produced by sample I. However, the "unacceptable" samples IV and V produce an output approximately a factor of 10 or more below that of sample I. Thus, a clear distinction between acceptable and unacceptable surfaces is obtained.

It can thus be seen that a fiber bundle with an LED light source is a practical system for monitoring the color of gold deposits on a production plating line. Of course other light sources can be used, such as a broadband source, typically tungsten, as noted in FIG. 3, with an appropriate filter or filters in the transmitted or reflected light paths to obtain the desired wavelength response. A filter having a transmission peak centered in the 450-575 nanometer range would typically be bluish-green, green, or yellowish-green. Alternately, two light sources of the appropriate wavelengths can be used in the embodiment of FIG. 3. In addition, various other detectors, such as phototransistors, photocells, photoresistors, etc., can be used instead of the photodiode listed in the above example.

Instead of, or in addition to, tailoring the source to produce the desired wavelengths, the wavelength response of the detector or the transmission spectrum of the optical fiber bundle can be used to obtain the desired overall wavelength response to the reflected light. The overall wavelength response of the system is obtained by integrating the product of the source output spectrum, the detector response spectrum, and the optical path transmission spectrum over a given wavelength range. As used herein, the "source output spectrum" is the optical power output of the source per unit wavelength as a function of wavelength, and the "detector response spectrum" is the output signal amplitude of the detector for a unit of incident illumination power as a function of illumination wavelength. The "optical path transmission spectrum" represents the transmissivity of the optical path as a function of wavelength, including the effects of filters and optical fibers, if any, but excluding the effects of the source, gold surface, and detector. For practicing the present invention, it is sufficient if the overall wavelength response in the range 450-575 nanometers is greater by at least a factor of 2 than the overall wavelength response for all wavelengths outside this range. The embodiment of the above Example has an overall wavelength response in the 450-575 nonometer range that is about a factor of 3 greater than its overall wavelength response to all wavelengths outside this range.

Numerous variations on the electronic measurement and comparison means may be made. As noted above, the comparator of FIGS. 2 and 3 may be a difference detector or a ratio detector, according to principles known in the art. Also, the source may radiate directly on the sample, with the reflected radiation being detected directly by means of the detector, without the use of an optical fiber in the optical path between the source, the sample, and the detector. If a reference surface is used, as in FIG. 2, it need not be bright gold, but can have a known degree of brown gold staining. The comparison then can be to determine, for example, whether the output of the inspection detector is greater than the output of the reference detector. In addition, to compensate only for certain effects such as changes in the output of the optical source or transmissivity of the optical path, the reference surface need not be gold, but can be another reflective substance.

Although the inspected surface is typically electroplated gold, other types of gold surfaces can be inspected, including electroless deposited gold, sputtered or evaporated gold, etc. The term "gold surface" includes gold alloy surfaces also. The present invention can be practiced on any surface containing a sufficient amount of gold that a detectable dip in the relative reflectivity in the 450-575 nanometer range is obtained when objectionable discoloration is present.

Furthermore, the condition of the gold surface as determined by the inventive method may be used in controlling the process used to form the gold surface or in other prior or subsequent processing steps. That is, the output of the inspection detector may be employed to control process parameters, including, for example, plating current density, plating solution concentration, etc. The sensitive, instrumented determination of surface conditions by the inventive method implies that such process control can correct many non-optimum conditions in a more nearly real-time manner than can current visual inspection techniques. This process control can be in lieu of, or in addition to, the use of the inventive technique as a pass/fail quality control check.

All such variations and deviations which basically rely on the teachings by which the present invention has advanced the art are considered to properly be within the spirit and scope of the present invention.

I claim

1. A method of making an article comprising the step of determining the condition of a gold surface on said article by steps comprising directing illumination from a source toward the inspected gold surface and detecting reflected light therefrom by means of an inspection detector, with said illumination thereby traversing an optical path between said source, said surface, and said detector, characterized in that the reflected light detected by said inspection detector is substantially in the wavelength range of 450 to 575 nanometers, and further characterized in that the amount of reflected light detected in said wavelength range is substantially determined by the degree of scattering of said illumination by said gold surface.

2. The method of claim 1 further characterized in that the overall wavelength response to the reflected light, obtained by integrating the product of the illumination spectrum, the inspection detector response spectrum, and the optical path transmission spectrum over a given wavelength range, is at least a factor of 2 greater for the range 450-575 nanometers than the overall wavelength response for all wavelengths outside this range.

3. The method of claim 1 further characterized in that said source is a light emitting diode having a peak output within the range 450-575 nanometers.

4. The method of claim 1 further characterized in that a filter having a transmission spectrum maximum in the wavelength range 450-575 nanometers is placed in said optical path.

5. The method of claim 1 further characterized by directing illumination towards a reference gold surface, detecting light reflected therefrom by means of a reference detector, and comparing the output of said inspection detector to the output of said reference detector.

6. The method of claim 1 further characterized by detecting by means of a reference detector light having wavelengths greater than 700 nanometers reflected from said surface, and comparing the output of said inspection detector to the output of said reference detector.

7. The method of claims 1, 2, 3, 4, 5, or 6 further characterized in that said optical path includes a bundle of parallel optical fibers which conducts illumination to the proximity of said inspected surface from said source, and which conducts said reflected light from the proximity of said inspected surface to said inspection detector.

8. The method of claim 7 further characterized in that the distance from the ends of said fibers to said inspected surface is such that the output of said inspection detector as a function of said distance is within 10 percent of the maximum output.

9. The method of claim 1 further characterized in that the output of said inspection detector is employed to control a parameter of a process used in forming said gold surface.

10. The method of claim 9 further characterized in that said parameter is plating current density or plating solution concentration.

* * * * *